US012654039B2

(12) United States Patent
Anquez et al.

(10) Patent No.: US 12,654,039 B2
(45) Date of Patent: Jun. 16, 2026

(54) METHOD, DEVICE, AND METHOD FOR USING OF A DEVICE TO COAGULATE VARICOSE VEINS WITH HIGH-INTENSITY FOCUSED ULTRASOUND

(71) Applicant: THERACLION SA, Malakoff (FR)

(72) Inventors: Jérémie Anquez, Paris (FR); Anthony Grisey, Saint Cyr l'Ecole (FR); Nesrine Barnat, Bezons (FR)

(73) Assignee: THERACLION SA, Malakoff (FR)

( * ) Notice: Subject to any disclaimer, the term of this patent is extended or adjusted under 35 U.S.C. 154(b) by 1053 days.

(21) Appl. No.: 17/619,681

(22) PCT Filed: Jun. 17, 2020

(86) PCT No.: PCT/EP2020/066778

§ 371 (c)(1),
(2) Date: Dec. 16, 2021

(87) PCT Pub. No.: WO2020/254417

PCT Pub. Date: Dec. 24, 2020

(65) Prior Publication Data

US 2022/0305297 A1     Sep. 29, 2022

(30) Foreign Application Priority Data

Jun. 19, 2019    (WO) .................. PCT/IB2019/000714

(51) Int. Cl.
*A61N 7/02*        (2006.01)
*A61B 8/00*        (2006.01)
(Continued)

(52) U.S. Cl.
CPC .............. *A61N 7/02* (2013.01); *A61B 8/0891* (2013.01); *A61B 8/463* (2013.01); *G06T 7/0012* (2013.01);
(Continued)

(58) Field of Classification Search
None
See application file for complete search history.

(56) References Cited

U.S. PATENT DOCUMENTS 8,214,052 B2    7/2012  Merchant, Jr.
2004/0122493 A1    6/2004  Ishibashi et al.
(Continued)

FOREIGN PATENT DOCUMENTS

WO        2006/129045 A2    12/2006
WO        2011/064209 A1     6/2011
(Continued)

OTHER PUBLICATIONS

Vaezy et al., "Use of high-intensity focused ultrasound to control bleeding". J. Vascular Surg. 1999; 29:533-42 (Year: 1999).*
(Continued)

*Primary Examiner* — Yi-Shan Yang
(74) *Attorney, Agent, or Firm* — Secant IP, PLLC

(57) ABSTRACT

The invention discloses a method and a device to treat vessels. In particular, the invention is directed at a method to occlude varicose veins while avoiding the formation of bubble clouds in the tissue surrounding the vessel and/or their interaction with the ultrasound beam. The invention is further directed at a device adapted to perform the method.

7 Claims, 3 Drawing Sheets

(51) Int. Cl.

| | |
|---|---|
| *A61B 8/08* | (2006.01) |
| *G06T 7/00* | (2017.01) |
| *G06T 7/10* | (2017.01) |
| *G06T 7/20* | (2017.01) |
| *G06T 7/70* | (2017.01) |
| *G06T 11/00* | (2006.01) |
| *A61N 7/00* | (2006.01) |

(52) U.S. Cl.

CPC .................. *G06T 7/10* (2017.01); *G06T 7/20* (2013.01); *G06T 7/70* (2017.01); *G06T 11/00* (2013.01); *A61N 2007/0004* (2013.01); *A61N 2007/0039* (2013.01); *A61N 2007/0086* (2013.01); *G06T 2207/10132* (2013.01); *G06T 2207/30004* (2013.01); *G06T 2207/30204* (2013.01)

(56) References Cited

U.S. PATENT DOCUMENTS

| | | | | |
|---|---|---|---|---|
| 2010/0094178 | A1* | 4/2010 | Lacoste ................... | A61N 7/02 |
| | | | | 601/2 |
| 2011/0009734 | A1* | 1/2011 | Foley ...................... | A61N 7/02 |
| | | | | 601/2 |
| 2012/0157842 | A1* | 6/2012 | Davis ...................... | A61B 8/08 |
| | | | | 600/439 |

FOREIGN PATENT DOCUMENTS

| | | | |
|---|---|---|---|
| WO | 2019110133 | A1 | 6/2019 |
| WO | 2020254417 | A1 | 12/2020 |

OTHER PUBLICATIONS

International Search Report and the Written Opinion of the International Searching Authority for International Application No. PCT/EP2020/066778 dated Aug. 18, 2020, 15 pages.

Y. Zhou et al., "Targeted Long-Term Venous Occlusion Using Pulsed High-Intensity Focused Ultrasound Combined with a Pro-Inflammatory Agent", Ultrasound in Medicine & Biology, vol. 37, No. 10, Jun. 16, 2011, pp. 1653-1658.

K. Hynynen et al., "Noninvasive Arterial Occlusion Using MRI-Guided Focused Ultrasound", Ultrasound in Medicine & Biology, vol. 22, No. 8, Jul. 1, 1996, pp. 1071-1077.

J.H. Hwang et al., "Targeted Venous Occlusion Using pulsed High-Intensity Focused Ultrasound", IEEE Transactions on Biomedical Engineering, 54(1), Jan. 2010, pp. 37-40.

J.H. Hwang et al., "Correlation Between Inertial Cavitation Dose and Endothelial Cell Damage In Vivo", Ultrasound in Medicine & Biology, vol. 32, No. 10, Jul. 11, 2006, pp. 1611-1619.

J.H. Hwang et al., "Vascular Effects Induced by Combined 1-MHz Ultrasound and Microbubble Contrast Agent Treatments In Vivo", Ultrasound in Medicine & Biology, vol. 31, No. 4, Dec. 17, 2004, pp. 553-564.

* cited by examiner

METHOD, DEVICE, AND METHOD FOR USING OF A DEVICE TO COAGULATE VARICOSE VEINS WITH HIGH-INTENSITY FOCUSED ULTRASOUND

The invention relates to a method, a device and a method of use for a device for treating vessels, in particular varicose veins, with High-Intensity Focused Ultrasound (HIFU) according to the features of the independent patent claims.

It is known to use heat treatments for the occlusion of veins, for example for the treatment of varicose veins.

U.S. Pat. No. 8,214,052 discloses an invasive method for treating a vein with a catheter which can deliver heat to the vein wall. The catheter is positioned within the vein segment to be treated, RF energy is applied to heat the vein wall and the catheter is withdrawn from the vein.

The main drawback of this method is that the catheter has to be invasively inserted in the vein segment to be treated, which carries a risk of perforation and is a complex process for tortuous veins.

HIFU devices allow the non-invasive treatment of targets within a patient's body. For focusing the HIFU device within the target zone, imaging of the area surrounding the target zone is performed, e.g. by means of MRI, ultrasounds, CT or optical means.

In particular, HIFU devices with an integrated B-mode ultrasound imaging device, as described exemplarily in WO 2006/129045 A2, are used.

Mechanical or thermal effects are described as potential mechanisms for HIFU treatments of veins. Mechanical effects rely on damaging the endothelium of the vessel to promote thrombus formation and induce occlusion. This method has not been proven to be efficient without adjuvants (Hwang et al. 2005, 2006, 2010; Zhou et al. 2011).

Thermal effects can also damage the endothelium but are more efficient since the damages may extend to the other layers of the vein wall (media, adventitia) and thermal denaturation of the collagen results in a beneficial lumen shrinkage. Other thermal methods (laser, radiofrequency) are now widely accepted.

HIFU thermal ablation is most effective when the blood flow is reduced to a minimum to avoid the heat sink effect.

A combination of both, mechanical and thermal effects was described in (Hynynen et al. 1996), where mechanical effects were used to induce a vasospasm, thus stopping the blood flow and putting the vessel in a favorable configuration for subsequent thermal pulses.

Hynynen et al. further state in context with the characteristics of the focal spot that the half-intensity beam diameter and length were 1.0 mm and 4.8 mm, respectively. The diameter of its target is described as the diameter measured from the x-ray angiograms which was about 0.6 mm. Hynynen et al. further disclose the idea of purposely damaging the tissues surrounding a blood vessel to occlude it.

In the following, "pulse" refers to the delivery of ultrasound energy into a tissue, in particular to achieve a treatment effect in said tissue, and "site" refers to the central position of the focal spot during a pulse. "Above" a structure refers to the portion of space which is between this structure and the HIFU transducer, "under" is defined accordingly. Thus, the "top" or the "superficial" part of the structure refers to the part of the structure which is closer from the HIFU transducer.

In Hynynen et al. 1996, a treatment plan was described where the pulses were delivered at positions forming a square of 4 by 4 sites, centered on the vein in a transverse plane.

In practice, the location of the sites with respect to the vein is critical. Indeed, if the pulses induce cavitation or boiling in the tissue located between the transducer and the vein, the bubble cloud will play the role of a strong reflector for subsequent pulses delivered at or close to the current site, thus making the lesions gradually grow pre-focally.

It is therefore the object of the present invention to overcome the drawbacks of the prior art and to provide an improved method for HIFU treatment of a hollow structure comprising a wall and a fluid in its uncompressed state, such as a blood vessel, in particular to provide a treatment method that avoids the creation of lesions outside of and ensures proper formation of a lesion in the targeted area.

This and other objects are solved by the method and device according to the independent claims of the present invention.

The method according to the invention is directed to the treatment of a hollow target by a HIFU beam having a focal spot. The focal spot, in particular the center of the focal spot, is positioned at a position that is further away, in particular deeper, or tangent to a target depth representing the position of the target, such as to avoid or limit the creation of a bubbles, in particular a bubble cloud, in tissue located between a treatment head and the target during the emission of a pulse.

In a particularly preferred embodiment, the HIFU beam is directed such that the center of the focal spot and/or a point of maximum intensity of the acoustic field is placed at a position at least tangent or deeper than the target.

Preferably, the center of the focal spot and/or the point of maximum intensity of the acoustic field referred to herein are measured in water as a reference.

A position deeper than the target may be understood as a position that, along an axis extending from a treatment head or transducer to the target, is closer to the target than the treatment head/transducer, but not between the treatment head/transducer and the target.

The target depth shall, in general, be understood as the location or position of the target, for example a vein wall. However, a target may have a thickness that is non-negligible compared to the focal spot size. In such cases, the target depth shall be understood as an any depth within the target such that the target depth represents the target. For example, if the target is a vein, the target level may be defined as the center of the vein, or the upper or lower boundary of a vein wall.

The distance with respect to the target depth can be chosen such that the formation of a bubble cloud in the tissue between the target and the treatment head is avoided or limited. In particular, the difference with respect to the target depth may be comprised in the range of 0 to 16 mm, preferably 0 to 12 mm, particularly preferably 0 to 8 mm. If cavitation and/or boiling are used as a primary mechanism for lesion formation, this can generate bubble clouds several millimeters above the focal spot.

A limitation of the formation of bubbles may in particular refer to bubbles formed by a first pulse that do not interfere with a second, later pulse. For example, if pulses are delivered with a lateral distance of 3 mm, a first pulse delivered at a first location may cause a bubble formation. If the bubbles formed by the first pulse are sized and located such that the next HIFU pulse, delivered at a second location 3 mm away from the first location, is not reflected by the bubble cloud, the formation of bubbles of the first pulse may have been sufficiently limited.

Thus, the range is particularly preferably 2 to 8 mm. In the case that boiling and/or cavitation are unlikely to be significant, the range is particularly preferably 0 to 2 mm.

Alternatively and/or additionally, the difference with respect to the target depth is comprised in the range of 10% and 200% of the focal spot length, preferably 20% and 100% of the focal spot length, most preferably 30% and 70% of the focal spot length.

For example, a practical implementation could include placing the focus so the superficial border of the focal spot is tangent to the superficial border of the vein wall. The distance could then be:

0 mm from the top of the focal spot to the top of the vein wall,

About half the size of the focal spot from the center of the focal spot to the top of the vein wall, typically 1 to 4 mm The values may differ depending on the target depth (the top of the vein, the middle of the vein etc.) and the definition of the focal spot.

Furthermore, an additional safety margin can be included. For example, this safety margin could be defined based on prior experiments quantifying the variability of the lesion size, or the variability of the hyperechoic mark size, and/or others. In this case, confidence intervals can be used to set the safety margin. For example, if the standard deviation of the HEM size above the focus is 1 mm, an additional safety margin of this value can be included in the distance between the target depth and the focal point.

The target comprises, in its uncompressed state, a wall and a liquid.

In particular, the invention provides a way of properly placing the sites with respect to the target in such a way as to avoid or limit the formation of bubbles in the tissue between the transducer and the vein.

If a bubble cloud is created in a soft tissue, the bubbles will be trapped in the tissue and the bubble cloud will act as a strong reflector for several seconds. The method relies on the fact that, by contrast, bubbles generated in a fluid, such as blood, will be removed rapidly after and during HIFU. This can occur due to dissolution, wash out, radiation force, or buoyancy. Nuclei may still be partially present at the next pulse but minimized by the effects above. By placing the site in an area where liquid such as blood is present, bubbles may be removed.

Inducing bubbles in the tissue below the target is not detrimental and could even be beneficial since a bubble cloud under the target would both shield the tissue underneath and reflect part of the energy to the target.

The sites may be placed according to certain criteria. In the following, the criteria are explained with respect to the "focal spot". The focal spot is commonly understood as the zone where the intensity is greater than −6 dB of the maximum intensity.

However, these criteria may also apply to other definitions and, in the following, the expression "focal spot" shall be understood as that zone around the point of maximum intensity of the acoustic field in the, in particular hypothetical, absence of interaction of the beam with preexisting bubbles, where cavitation or boiling may occur in the tissue under the conditions of the treatment (power, pulse durations, etc.). These notions can refer to an actual zone (e.g. actual −6 dB focal spot in the tissue), or an estimation based on measurements in a testing environment, in particular in water, computations based on the geometry, simulations, experiments etc. As known by the person skilled in the art, bubble clouds may significantly grow above the focus, causing what is commonly called a "tadpole-shape lesion", and significant bubble activity can sometimes be detected mainly above the focus.

If the target is compressible, the methods of the invention are more efficient when the target is not or only partially collapsed. If the target is a vein, it is preferably partially collapsed. However, the methods may also be applicable when the target is completely collapsed. In this case, there is no fluid inside the target but, to avoid the target being shielded by bubble clouds, the pulses are preferably delivered below the target.

The "top" of the focal spot (the border which is located towards the transducer) can be tangent to the upper border of the target (the border which is closer to the transducer).

In a preferred embodiment, the target depth is the depth of the superficial part of the target wall.

In another preferred embodiment, the target depth hence is the depth of the part of the target wall positioned away from the treatment head or the center of the target lumen.

Preferably, the distance between the focal spot and the target depth is increased by a safety margin.

For example, the top of the focal spot may be placed below the lower border of the target. This is of particular interest when the pulses induce cavitation or boiling before the end of the pulses. In this case, the reflection induced by the bubble cloud present at focal spot induces a strong pre-focal heat deposition during the pulse, which may induce undesired cavitation or boiling above the target, in particular if the focal spot is too high.

Preferably, an additional safety margin is taken to account for the variability in tissue characteristics. In this case, the top of the focal spot is located at a predefined distance to the upper border of the target. This distance is typically between $\lambda/5$ and $10\times\lambda$, wherein $\lambda$ represents the wavelength of the HIFU pulse. Additionally or alternatively, the safety margin can also be defined based on the variability of the size of the generated bubble cloud or the induced lesion, which can for example be measured, simulated, estimated, or known from prior experiments.

In yet another preferred embodiment, the target depth is defined as the depth of the superficial part, the center of the target lumen, or the deep part of of the target wall increased by a safety margin. In particular, the safety margin can be defined as a percentage of the lumen wall thickness or focus spot size. Preferably, it is comprised in the range of 0 to 5 mm, even more preferably 0.1 to 1 mm.

These methods also apply in presence of an infiltration (for example, a tumescent anesthesia). In this case, the distances may also be, but are not necessarily, implemented with respect to targets related to the zone filled with the injected liquid. For example, the applied rule may be to always position the top of the focal spot beyond the upper border of the zone filled with the injected liquid. In a preferred embodiment, the target depth is hence defined as the depth of the superficial part of a zone filled with fluid due to an infiltration.

In another preferred embodiment, the target depth is defined as the depth of the superficial part of a zone filled with fluid due to an infiltration, increased by a safety margin.

In practice, this distance from the target depth is preferably implemented based on a segmentation of the target, either automatic or manual, on acquired images. Preferably, it is done based on A-mode, B-mode, color Doppler, Duplex ultrasound or Magnetic Resonance imaging. It can also be based on passive or active cavitation, bubble detection algorithms: for example, after delivering a pulse designed to only induce cavitation in the blood (since it is easier than in the tissue), it is possible to determine the position of vein based on a cavitation map.

In a preferred embodiment, the target depth is determined for each treatment site based on an automatic segmentation algorithm. For example, the vein can be easily segmented when it is not compressed based on the fact that the lumen is hypoechoic and free of speckle. If it is at least partially compressed, one may take advantage of a segmentation of the open vein and follow it using a speckle tracking algorithm or based on anatomical landmarks (fascia, bone etc.).

In a preferred embodiment, this safety margin varies depending on the characteristics of the pulse (duration, power, shape of the beam . . . ). Preferably, it increases when the power or the duration is increased. Preferably, this variation is automatic, based on a priori knowledge based on prior experiments, simulations or measurements.

In an alternative preferred embodiment, the target depth is determined for each site based on a manual segmentation of the target. Alternatively, it can be based on manual placement of one or several markers on the live image.

Placing the focal spot according to one of these criteria is likely to damage the tissues located under the target. This shall not be considered detrimental since the contraction of the surrounding tissues may compress the structure and improve the treatment outcome.

In another preferred embodiment, a marker representing a position related to the focal spot, is overlaid on a monitoring image and the position of the focal spot with respect to the target is adjusted before each pulse, typically by the user.

In particular, a marker can be overlaid to the monitoring image and the user may place the focal spot, so that, for example, the marker is below the upper border of the target, as seen on the image.

Additionally or alternatively, at least one marker representing a range along the ultrasound propagation axis is overlaid on a monitoring image. The range represents locations where the target should be.

In a preferred embodiment, the focal spot is placed such that the tissue located deeper than the target is damaged by the pulse, and the tissue located above the target is damaged less than the tissue above the target. Preferably, the tissue located above the target is not damaged at all.

Under certain circumstances, a bubble cloud may still be formed even if the method according to the invention is performed due to statistical fluctuations, for example due to local tissue characteristics). In particular, even when the proposed device or methods are applied, a bubble cloud may be generated above the target. In this case, it is advantageous to adapt the spacing between several treatment sites to avoid the shielding effect. Thus, alternatively or additionally, the invention also provides and is directed to a method of modifying the direction or position of the HIFU beam when a bubble cloud is detected. Detection of a bubble cloud can be automatic by continuous or repeated monitoring. The modification of the HIFU beam then also can be automatic, based on the results of the monitoring. In an alternative embodiment, the modification can occur based on a manual detection of the bubble cloud.

Another method according to the invention hence may also comprise monitoring if a bubble cloud which may interact with the HIFU beam in the soft tissue is located above the target. If such a bubble cloud is detected, the method comprises modifying the location of the focal spot of a HIFU pulse.

In a preferred embodiment, the modification of the location of the HIFU pulse occurs based on a manual detection of the bubble cloud.

Preferably, when a bubble cloud is visible above the target, or above a certain depth defined with respect to the target, the lateral spacing between treatment sites is increased so that the bubble cloud is not within the ultrasound beam. An additional safety margin can also be used to account for diffraction and variability in tissue properties.

In a preferred embodiment, the modification occurs based on an automatic detection of the bubble cloud.

A bubble cloud detection algorithm for automatically detecting the bubble cloud may be employed. In particular, this is advantageous if the monitoring is based on B-mode imaging and the bubble clouds are induced by boiling. Because bubble clouds induced by boiling appear as hyperechoic marks, which are easy to detect, especially when comparing the image after the pulse with at least one image captured before the pulse. The comparison can be conducted by an algorithm, in particular an algorithm as disclosed in EP 2 599 444.

In particular, an overlay may be used. An overlay shall mean a means for displaying graphic depiction place on a live and/or acquired ultrasound image, preferably a marker. For example, an overlay may comprise a representation of the focal spot and/or different markers to indicate treatment characteristics and/or a delineation of some anatomical structure.

In a preferred embodiment, based on the position and size of one or several bubble clouds generated by one or several previous pulses with respect to the target, the safety margin regarding the position of the focal spot is adapted or another characteristics of the pulse (power, duration, shape of the beam . . . ) is adapted. For example, for the first pulse, the −6 dB focal spot may be manually positioned to be tangent to the upper border of the vein, based on appropriate overlay on the live image indicating the position of the focal spot. Based on prior experiments, the induced bubble cloud is supposed to extend 2 mm above the target, which would not negatively impact subsequent pulses. After delivering this pulse, the bubble cloud is automatically segmented based on the B-mode image. It appears that the bubble cloud extends 4 mm above the target, as a result of the local characteristics of the tissue and the parameters of the pulse. As a consequence, the safety margin is automatically increased from 0 mm to 2 mm to compensate for this unexpected growth of the bubble cloud above the target. The overlay is modified to include a marker indicating that the upper border of the focal spot should be placed 2 mm under the upper border of the vein. For example, a small segment is displayed 2 mm above the representation of the focal spot.

In an alternative preferred embodiment, the modification is triggered by the user. In particular, the user may manually trigger an increase a lateral spacing between treatment sites, by manually placing the next site, or by a simple interaction (button) on the user interface, which automatically adds a predefined value to the spacing.

Alternatively, the lateral spacing is defined prior to the treatment based on a priori knowledge of the size of the bubble clouds induced by the pulses.

In particular, the lateral spacing within one segment may vary within a range.

If the monitoring mean gives only a 2D information, which is the case for a conventional B-mode imager, the imager is preferably rotated or moved orthogonally to the imaging plane to obtain a 3D information on the position of the bubble clouds and to adapt the spacing as described above.

In a preferred embodiment, the location of the pulse is modified by moving the beam about orthogonally to the main ultrasound propagation axis so the HIFU beam is tangent to or does not substantially intersect the bubble cloud.

In another preferred embodiment, the location of the pulse is modified by moving the beam about orthogonally to the main ultrasound propagation axis by a distance such that the HIFU beam and the bubble cloud are separated by a safety margin.

The implementation of the above methods may be difficult in practice since several concurrent factors have to be adjusted, comprising the vein compression and the position of the focal spot. According to another aspect, the invention is hence further directed to a device to perform an ultrasound treatment, in particular a HIFU treatment addressing this difficulty.

The invention further relates to a device.

The ultrasound treatment device, in particular the HIFU treatment device, comprises a probe head. The probe head has an ultrasound transducer for delivering treatment ultrasound waves focused onto a target within an object. The device further has an imaging device for imaging of the object, preferably within the treatment head, comprising a display. The device comprises a controller unit that is operatively connected to the transducer for controlling the emission of HIFU pulses, and optionally to the actuator and the compression unit. The display is adapted to overlay at least one marker on a monitoring image. The marker represents a location related to the focal spot and/or a range along the ultrasound propagation axis where the target should be.

It may further comprise a compression unit for applying a compression force to the object, and/or an actuator which allows for moving the probe head at least along the main ultrasound propagation axis or about orthogonally to the patient skin.

Preferably, to avoid lateral movements which could be dangerous for the patient, the actuator is controlled to move along the main ultrasound propagation axis or about orthogonally to the patient's skin.

The device is particularly adapted to allow for a manual positioning of the focal spot of the HIFU treatment transducer in the vicinity of the target. The device may additionally or alternatively be adapted to allow the user to indicate the position of the target or the desired position of the focal spot, or a range of acceptable positions. The device may also be adapted to automatically adapt the position of the focal spot based on an image tracking algorithm using the controller unit to pilot the actuator and the compression unit.

In particular, the device comprises a memory and is adapted to save in said memory a target depth (or a range) representing the zone where the target should be with respect to the focal spot. It may further comprise a display of overlays to help the user to properly place the focal spot with respect to the vein (e.g. overlay of the focal spot, overlay of a marker which depicts where should be some anatomical structure (e.g. the deep wall of the target), or a range in which the target should be. Finally, the device may be adapted to automatically position the focal spot based on the position of the vein and an automatic segmentation algorithm which enables to follow in real time the position of the target with respect to the focal spot as its position is adapted (speckle tracking, or based on automatic segmentation of the vein or anatomical landmarks.

Preferably, the treatment device is hence such that the user can roughly place the focal spot near the desired position and the device automatically refines the focal spot position and, optionally, the level of compression of the target or other factors.

Refinement can be performed based on an optimization algorithm. In this context, a cost function can be defined to quantify the "distance" between the actual state and the desired state, a "state" being characterized by the position of the focus and, optionally, the collapsing state of the vein and possible other factors. Then, an optimization algorithm (gradient method, Newton, metaheuristic method . . . ) can be used to adjust the parameters so as to minimize the cost function.

An image tracking algorithm which only tracks a vein may not be sufficient because a vein may be in a completely collapsed state. For example, this may be the case if the treatment head is pushed towards the skin and induced a pressure on the anatomy. Thus, the algorithm may comprise a speckle tracking algorithm. Such an algorithm also takes into consideration the context of the vein such as the surrounding tissue.

In a preferred embodiment, the compression unit comprises a membrane mounted onto the probe head. The membrane defines a cavity which can be filled with a fluid.

The fluid ensures acoustic coupling, for example as disclosed in WO2011064209A1. A pumping system enables circulating the fluid from a reservoir to the membrane, in a closed circuit. At least one controller unit enables the control of the fluid circulation according to at least one rule (for example, constant fluid pressure within the membrane or constant fluid volume within the balloon). This controller may be the same controller as mentioned above or also a separate independent controller. Appropriate sensors (for example, a pressure sensor within the balloon) are provided for controlling operation of the pumping system.

The ultrasound probe and the treatment transducer may be embedded into a probe head which is held by an actuator. Preferably, the actuator can move at least along the main ultrasound propagation axis or about orthogonally to the patient skin.

The fluid is circulated by a pumping system. The pumping system is operable in at least two operating modes by the controller unit. In a first operating mode of the controller unit, the pressure of the fluid in the cavity is controlled such that when the transducer is moved orthogonally to the skin or along the main ultrasound propagation axis by a given distance, a displacement of the focal spot by about the same distance and along the same direction within the anatomy is induced. In the first mode, moving the transducer translates to moving the focal spot by about the same amount within the anatomy. The fluid pressure remains fix.

In a second operating mode of the controller unit, the pressure is controlled such that when the transducer is moved orthogonally to the skin or along the main ultrasound propagation axis, a compression of the target but no significant change of depth of the focal spot under the skin is induced. The fluid volume within the balloon remains fix.

The two operating modes allow for performing a method as described below.

The treatment device may also comprise at least one monitoring means, for example, an ultrasound probe, and a display and a mean for the operator to interact with the display, for example a touchscreen.

The invention is further directed to a method of use of the device disclosed above.

In a first step, the treatment transducer is manually placed such that the focal spot is in the vicinity of the target and the target is within the field of view of the monitor. The target or the desired position of the focal spot or an acceptable range of positions is then graphically marked on a display. Additionally, the device is let to refine the parameters of the compression unit and move the transducer to adequately place the focal spot. Preferably, the device is adapted to automatically refine the parameters (for example, pressure within the coupling fluid, and/or feedback loop parameters) and moves the transducer in order to place the focal spot at the desired position and compress the target to the desired level. In particular, the operator may place the treatment transducer and/or outline the target or the desired position of an acceptable range of position of the focal spot. Additionally or alternatively, the device may compute the position of the target within the anatomy based on a tracking algorithm which uses the position drawn by the operator as the target position.

For example, the step of automatically refining the parameters of the compression unit may be performed by iteratively adapting the focal spot position in the anatomy by moving the actuator while the fluid control is in a pressure-controlled mode and compressing the target while the fluid control is in a volume-controlled mode.

The step of outlining the target or the desired position or an acceptable range of positions of the focal spot may also be omitted and the position of the target automatically be detected by a software without operator input. In particular, an automatic segmentation algorithm based on the contrast between the lumen of the vein and the surrounding tissue can be used. The latter is hypoechoic. Detection is preferably performed near the focus, either in a predefined zone around the focus, or by penalizing the distance to the focus.

The invention is further directed to a method of using an ultrasound device, in particular a HIFU treatment device. The device comprises a hand-held probe head which comprises an ultrasound transducer for delivering treatment ultrasound waves focused onto a target within an object and an imaging device for imaging of the object. A controller unit operatively connected at least to the probe head and to a compression unit. A compression unit is provided for applying a compression force to the object. The compression unit further comprises a membrane mounted onto the probe head which is filled with a fluid which is circulated by a pumping system. The controller unit is adapted to control the pumping system and the compression force by switching between at least two operating modes. In a first operating mode (R1) of the controller unit, moving the transducer orthogonally to the skin or along the main ultrasound propagation axis by a given distance induces a displacement of the focal spot by about the same distance and along the same direction within the anatomy. In a second operating mode (R2) of the controller unit, moving the transducer orthogonally to the skin or along the main ultrasound propagation induces a compression of the target but no significant change of depth of the focal spot under the skin. The method of using the described device includes controlling the compression force and the pumping system such that positioning the focal spot is performed in the mode R1 and adjusting the compression of the target is performed in the mode R2.

In a preferred embodiment, the method further comprises a feedback loop, wherein the steps positioning of the focal spot and the adjusting of the target compression are alternatingly repeated. In particular a feedback loop can be used to facilitate the focal spot positioning and comprises the following steps:

i.) the fluid circulation is controlled according to the rule R1, which enables easy positioning of the focus.

ii.) the fluid circulation is switched to the rule R2, which enables to compress the target without significantly changing the position of the focal spot within the anatomy.

Several iterations can be performed if needed to precisely adjust the position of the focal spot.

Alternatively, a third step iii.) can be implemented where the fluid circulation is switched into a mode where the fluid pressure is kept constant at the current value, which may be high since the device was controlled according to the rule R2 during step ii.).

In the following the invention is described in detail by reference to the following figures:

FIG. 1 schematically shows the effect of a bubble cloud interacting with the ultrasound beam.

FIG. 2 schematically illustrates a working principle of a method according to the invention in which the interaction between the bubble cloud and the ultrasound beam is avoided.

FIG. 3 schematically illustrates the location of the focal spot with different safety margins.

FIG. 4 schematically illustrates a working principle of the method according to the invention in which the interaction between the bubble cloud and the ultrasound beam is avoided from the top.

Figure 1:
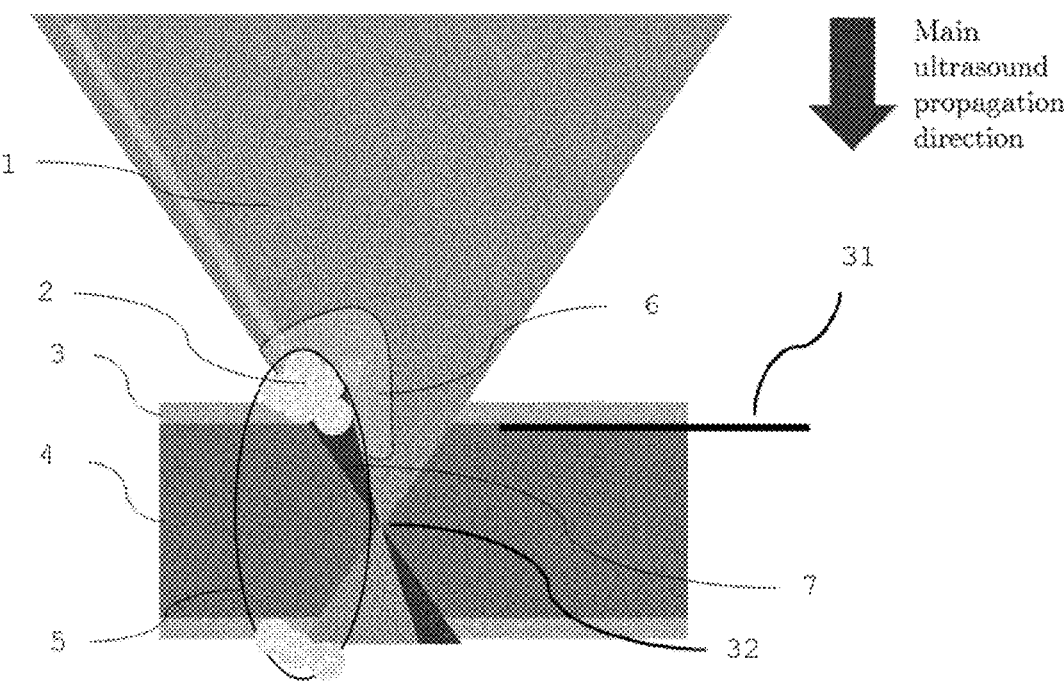

FIG. 1 shows the working principle of the method according to the invention and illustrates the object of the invention. A HIFU treatment is delivered to a target comprising a wall 3 and a lumen 4. In order to avoid the formation of a bubble cloud in an area 2 between the target 3,4 and a treatment head, the focus 32 of the HIFU beam is placed lower than a target level 31 in the direction of the ultrasound propagation. In this example, the target level is chosen to be the inner surface boundary of the target wall 3. However, it is also possible to use the outer surface level or the center of the target wall 3. The lower focus 32 allows for the treatment without the formation of a new bubble cloud.

However, it is possible that a previous pulse 5 has generated a bubble cloud in the area 2 which interacts with the ultrasound beam 1. This interaction creates a zone where heating is increased 6 and a zone which is shadowed 7.

Figure 2:
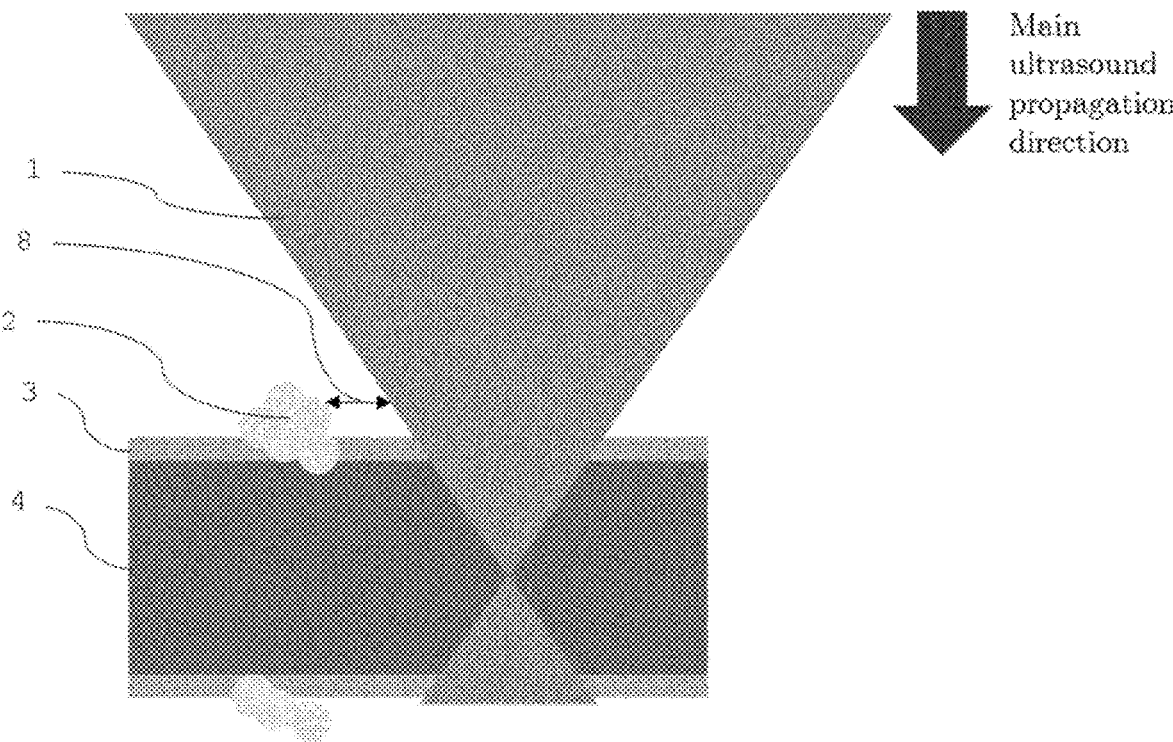

FIG. 2 shows schematically a preferred embodiment of a method according to the invention. During the treatment of a target comprising a wall 3 and a lumen 4, the HIFU beam 1 is located such that no bubble cloud is expected to be created in the tissue above the target. However, a bubble cloud has formed in an area 2 in a previous HIFU emission step (not shown) and is detected. Because the present bubble cloud in the area 2 may interact with the HIFU beam 1, the location of the HIFU beam is modified by laterally moving by an appropriate distance 8 to avoid the interaction.

Figure 3:
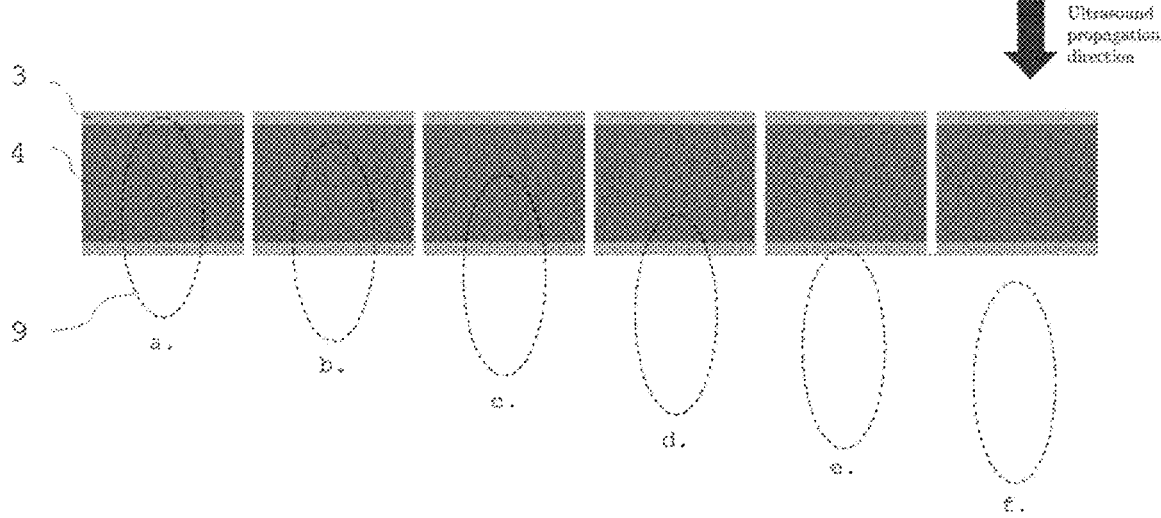

FIG. 3 shows how in the context of a treatment of a target comprising a wall 3 and a lumen 4, the focal spot 9 is tangent to the more superficial border of the target (FIG. 3a), to the center of the target (FIG. 3c), or the deeper border of the target (FIG. 3e). Additional safety margins can be taken (FIGS. 3b, 3d, and 3f). Although not explicitly shown in the figure, the person skilled in the art will recognize that other locations for the focal spot, in particular locations in between the illustrated cases, are possible. For example, the focal spot may be tangent to the outer surface level of the upper wall, or the inner surface level of the upper wall. In all cases the soft tissue located deeper than the target is damaged. As a general rule, the deeper with respect to a target level the focus spot 9 is located, the less probable the formation of a bubble cloud in the tissue above the target wall 3 is. However, with increasing depth, the treatment effect on the target wall 3 becomes smaller. Thus, the focal spot should be located as deep as necessary to avoid the formation of bubble clouds, but as close to the target level as possible.

Figure 4:
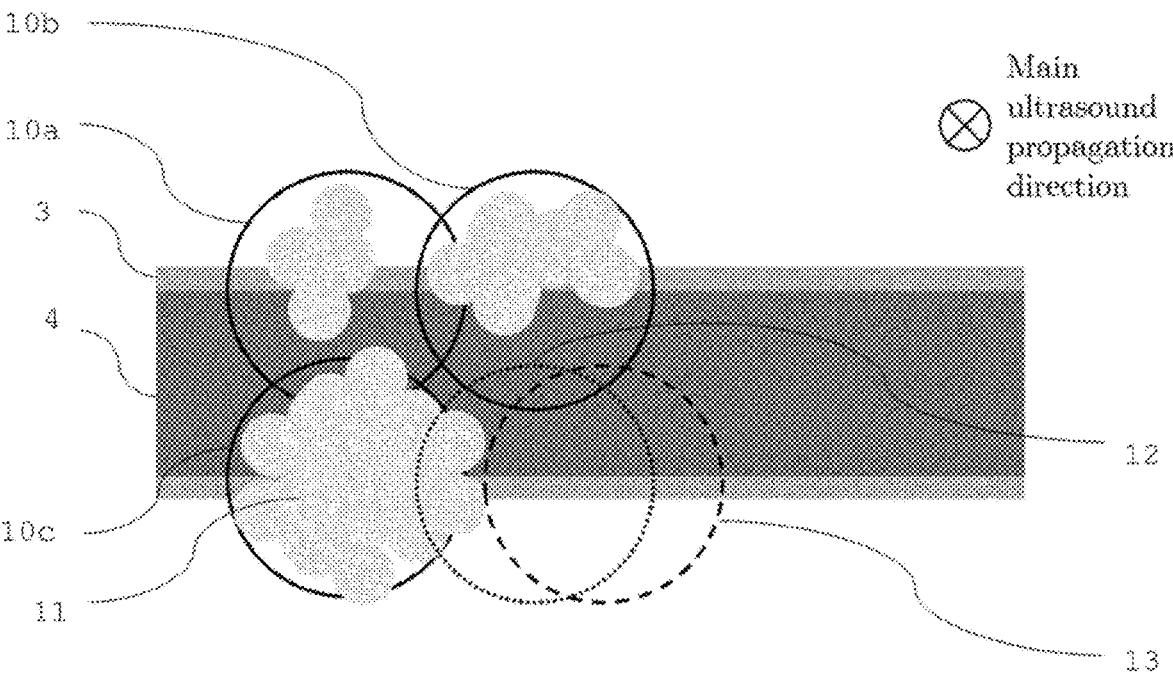

FIG. 4 illustrates a treatment in a plane perpendicular to the propagation axis of the HIFU beam. In the context of a treatment of a target comprising a wall 3 and a lumen 4, the previous pulses 10a, 10b, and 10c have generated bubble clouds 11 which extend into the soft tissue located above the target. When positioned at the planned site 12, the imaging probe is rotated to assess the bubble clouds 11 generated by the previous pulses 10a-10c. Since the bubble cloud 11 would interact with the HIFU beam (not shown), the site is move to another position 13.

Figure 5:
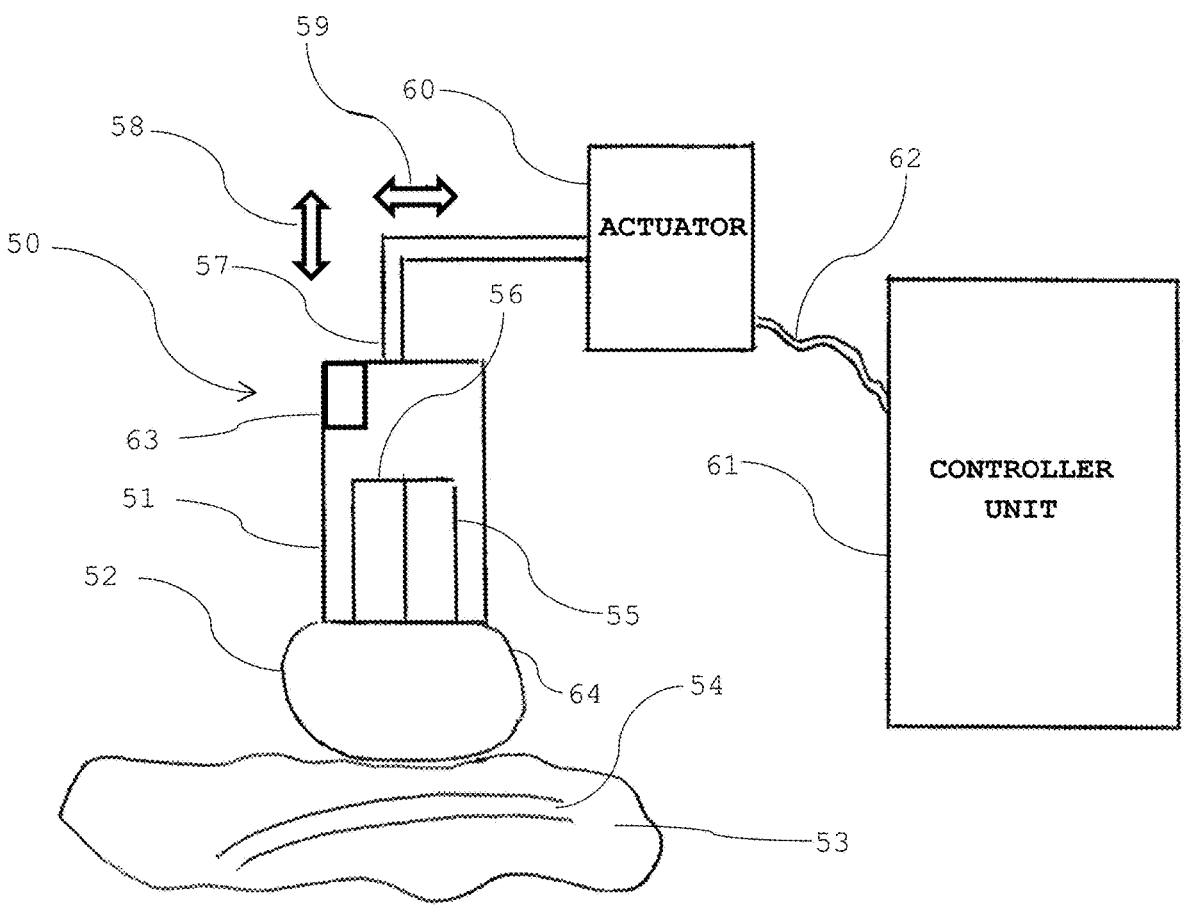
FIG. 5 shows a schematic depiction of a ultrasonic device according to the invention.

FIG. 5 shows schematically a device 50 according to the invention to treat a patient with HIFU. The device 50 comprises a probe head 51 with a treatment transducer 55. The transducer is adapted to deliver ultrasound waves focused onto a target 54 in an object 53. In the present embodiment, the treatment head 51 further comprises an imaging device 56. The treatment head further comprises a compression unit 52, here in the form of a membrane 64 that is mounted onto the probe head 51 and forms a cavity for receiving a fluid. The fluid in the cavity is circulated by a pumping system 63. The device further comprises an actuator 60 that is connected to the probe head 51 by an arm 57 and that is adapted to move the treatment head 51 along the main ultrasound propagation axis 58 and orthogonally to the patient skin 59. The device also comprises a controller unit 61 that is operatively connected to the transducer 55, the compression unit 52 and the actuator 60, in the present example by means of a cable 62.

Figure 6:
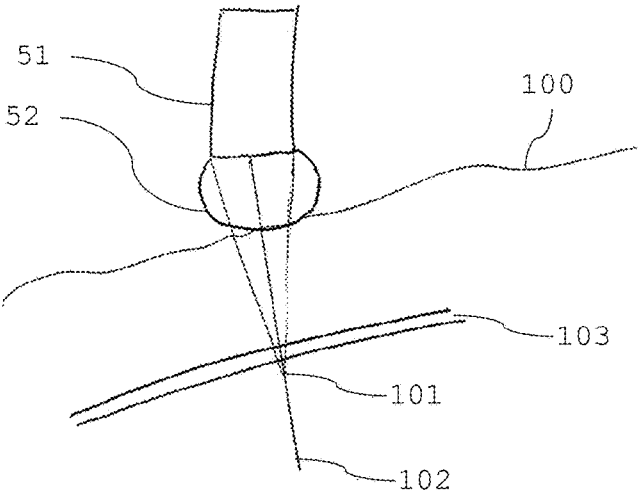
FIG. 6 shows schematically an orientation of a focus point with respect to a target and a treatment head.

FIG. 6 shows schematically a treatment head 51 as shown in FIG. 5 with a balloon 52 placed on a patient's skin 100 such as to treat a target 103. The center of the focal point 101 is placed at a position deeper than the target. For illustration, an axis 102 is shown that extends from the treatment head 51 through the target 103. The center of the focal spot 101 is further away from the treatment head 51 than the target, i.e. a distance between the treatment head 51 and the center of the focal spot 101 is larger than a distance between the target and the treatment head 51. Accordingly, the center of the focal spot 101 is not placed between the target 103 and the treatment head.

The invention claimed is:

1. A method for treatment of a vein by a HIFU beam having a focal spot, the HIFU beam being emitted by a treatment head, comprising positioning the treatment head so that a center of the focal spot is positioned or positionable deeper than a center of the vein, and further emitting a HIFU pulse with the center of the focal spot being deeper than the center of the vein, and further so that an upper boundary of the focal spot is at or deeper than an upper boundary of the vein, so that a creation of bubbles in a first tissue located between the treatment head and the vein is avoided or limited during the emission of the HIFU pulse.

2. The method according to claim 1, further including positioning the center of the focal spot, during the emission of the HIFU pulse, on a deep wall of the vein.

3. The method according to claim 1, further including applying an automatic segmentation algorithm to an acquired image, and positioning the center of the focal spot for each treatment site based on the automatic segmentation algorithm.

4. The method according claim 1, further including displaying a monitoring image, and overlaying a marker representing a location related to the focal spot to the monitoring image, further including adjusting the position of the center of the focal spot with respect to the vein before the emission of the pulse.

5. The method according to claim 1, including positioning the center of the focal spot is placed such that a second tissue located deeper than the vein is damaged by the pulse, and the first tissue located above the vein is damaged less than the second tissue deeper than the target.

6. The method according to claim 1, further including positioning the center of the focal spot, during the emission of the HIFU pulse, deeper than a deep wall of the vein.

7. A method for treatment of a vein by a HIFU beam having a focal spot, the HIFU beam being emitted by a treatment head, comprising positioning the treatment head so that a center of the focal spot is positioned or positionable deeper than a center of the vein, and further emitting a HIFU pulse with the center of the focal spot being deeper than the center of the vein, so that a creation of bubbles in a first tissue located between the treatment head and the vein is avoided or limited during an emission of the HIFU pulse, and so that tissue underneath the center of the vein is damaged more than tissue above the center of the vein.

* * * * *